US012622598B2

(12) United States Patent
Levin et al.

(10) Patent No.: US 12,622,598 B2
(45) Date of Patent: May 12, 2026

(54) DECREASING IEGM HAZARDS IN TIME DIVISION MULTIPLEXED SYSTEM

(71) Applicant: BIOSENSE WEBSTER (ISRAEL) LTD., Yokneam (IL)

(72) Inventors: Michael Levin, Haifa (IL); Alek Vilensky, Netanya (IL); Amit Yarimi, Yokneam (IL); Rami Rozen, Atlit (IL); Yavgeny Bonyak, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 16 days.

(21) Appl. No.: 18/084,832

(22) Filed: Dec. 20, 2022

(65) Prior Publication Data
US 2024/0197198 A1 Jun. 20, 2024

(51) Int. Cl.
*A61B 5/06* (2006.01)
*A61B 5/00* (2006.01)
*A61B 34/20* (2016.01)

(52) U.S. Cl.
CPC ............ *A61B 5/061* (2013.01); *A61B 5/7225* (2013.01); *A61B 34/20* (2016.02); *A61B 2034/2051* (2016.02)

(58) Field of Classification Search
CPC ....... A61B 5/061; A61B 5/7225; A61B 34/20; A61B 2034/2051
See application file for complete search history.

(56) References Cited

U.S. PATENT DOCUMENTS

| | | | |
|---|---|---|---|
| 5,391,199 | A | 2/1995 | Ben Haim |
| 5,443,489 | A | 8/1995 | Ben Haim |
| 5,558,091 | A | 9/1996 | Acker |
| 6,172,499 | B1 | 1/2001 | Ashe |
| 6,239,724 | B1 | 5/2001 | Doron |
| 6,332,089 | B1 | 12/2001 | Acker |
| 6,484,118 | B1 | 11/2002 | Govari |
| 6,618,612 | B1 | 9/2003 | Acker |
| 6,690,963 | B2 | 2/2004 | Ben Haim |
| 6,788,967 | B2 | 9/2004 | Ben Haim |
| 6,892,091 | B1 | 5/2005 | Ben Haim |
| 7,536,218 | B2 | 5/2009 | Govari |
| 7,756,576 | B2 | 7/2010 | Levin |
| 7,848,787 | B2 | 12/2010 | Osadchy |
| 7,869,865 | B2 | 1/2011 | Govari |

(Continued)

FOREIGN PATENT DOCUMENTS

CN 113206714 A 8/2021

OTHER PUBLICATIONS

Bui-Van, H. et al. 2017. Main beam modeling for large irregular arrays. Exp Astron. 44:239-258 (Year: 2017).*

(Continued)

*Primary Examiner* — Anh Tuan T Nguyen
*Assistant Examiner* — Dean N Edun

(57) ABSTRACT
In one embodiment, a medical system includes a catheter interface comprising electrode lines configured to be electrically connected to respective electrodes of a catheter, and a signal generation apparatus configured to generate signal pulses, each of the signal pulses comprising a carrier frequency and having a non-rectangular signal envelope, the signal generation apparatus being configured to time multiplex the signal pulses among the electrode lines.

8 Claims, 3 Drawing Sheets

(56) References Cited

U.S. PATENT DOCUMENTS

| | | | |
|---|---|---|---|
| 8,005,539 B2 | 8/2011 | Burnes et al. | |
| 8,456,182 B2 | 6/2013 | Bar-Tal | |
| 2017/0164867 A1* | 6/2017 | Kassab | A61B 5/6853 |
| 2018/0344392 A1* | 12/2018 | Montag | A61B 5/4836 |
| 2020/0093397 A1* | 3/2020 | Sra | A61B 6/485 |
| 2022/0095980 A1* | 3/2022 | Scharf | A61B 5/265 |
| 2022/0249849 A1 | 8/2022 | Qiao et al. | |
| 2022/0249850 A1 | 8/2022 | Qiao et al. | |

OTHER PUBLICATIONS

Wikipedia Article. 2021. Sigmoid Function. Accessed via WayBackMachine (Year: 2021).*
Wikipedia Article. 2021. Error Function. Accessed via WayBackMachine (Year: 2021).*
Invitation to Pay Additional Fees received for PCT Application No. PCT/IB2023/061783, mailed on Mar. 14, 2024, 28 pages.

* cited by examiner

Fig. 3                                                                    60
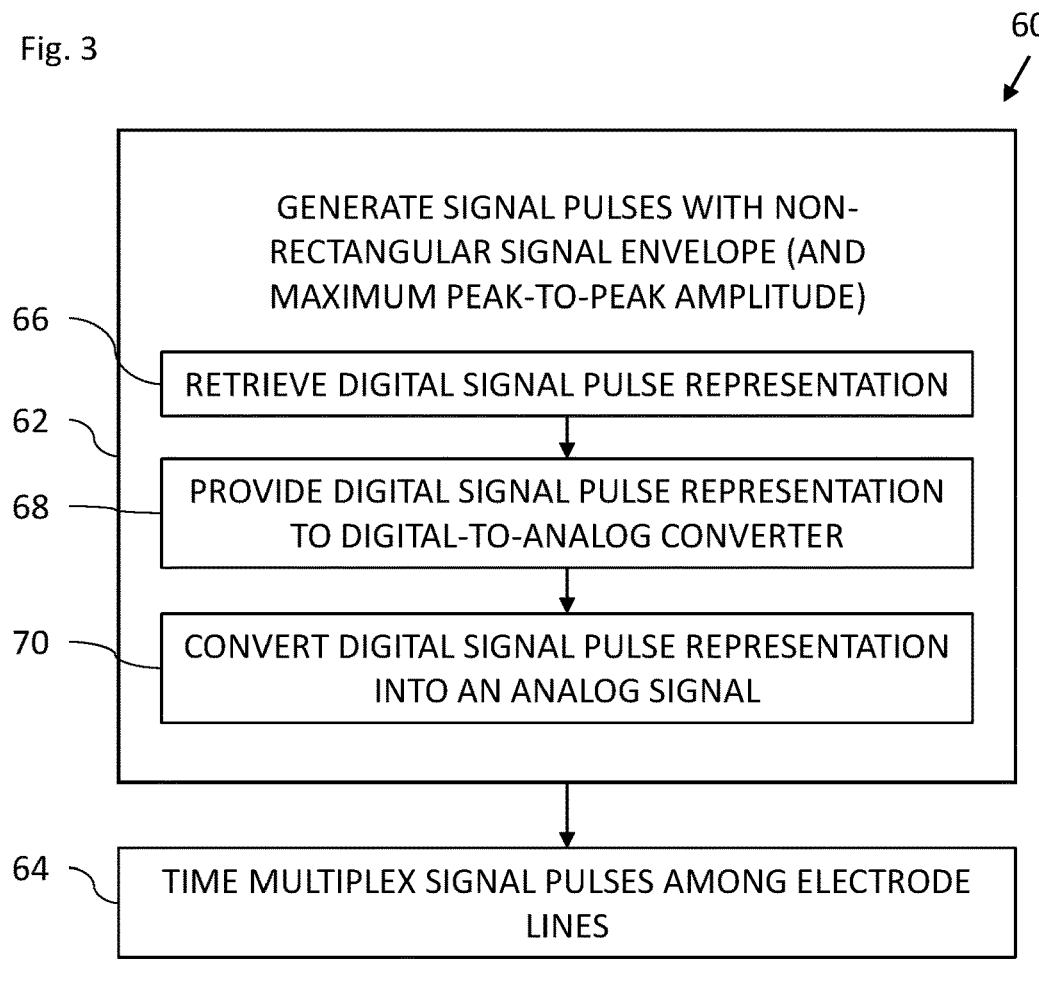
66 — GENERATE SIGNAL PULSES WITH NON-RECTANGULAR SIGNAL ENVELOPE (AND MAXIMUM PEAK-TO-PEAK AMPLITUDE)
62 — RETRIEVE DIGITAL SIGNAL PULSE REPRESENTATION
68 — PROVIDE DIGITAL SIGNAL PULSE REPRESENTATION TO DIGITAL-TO-ANALOG CONVERTER
70 — CONVERT DIGITAL SIGNAL PULSE REPRESENTATION INTO AN ANALOG SIGNAL
64 — TIME MULTIPLEX SIGNAL PULSES AMONG ELECTRODE LINES
Fig. 4                                                                    80
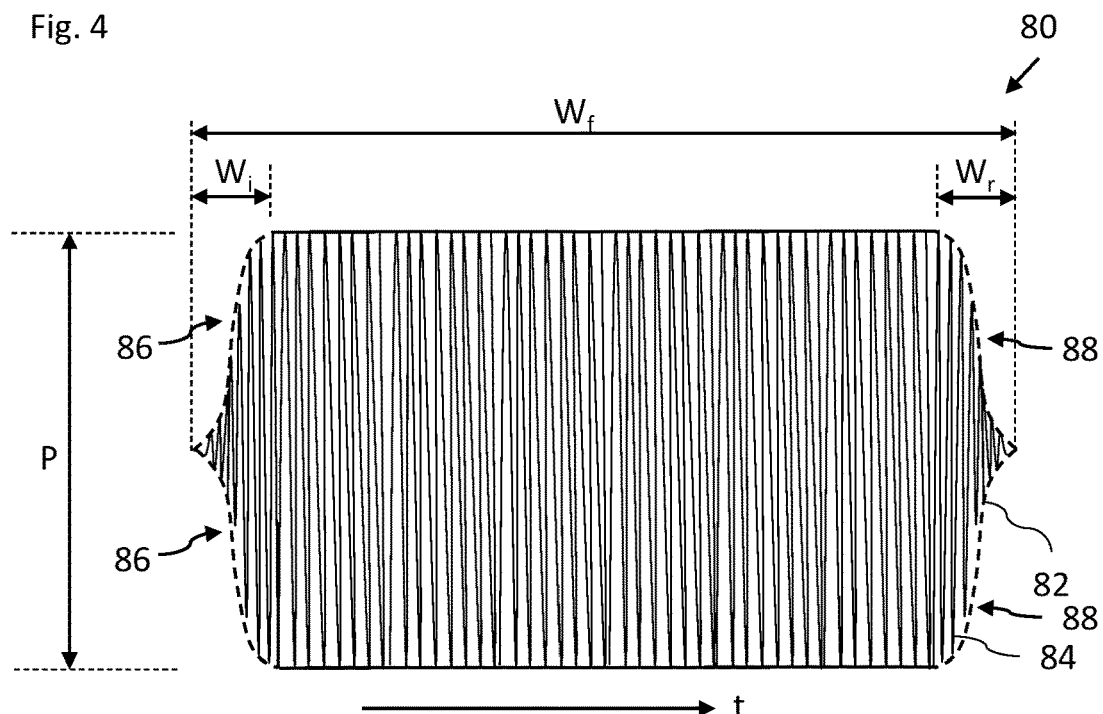

DECREASING IEGM HAZARDS IN TIME DIVISION MULTIPLEXED SYSTEM

FIELD OF THE DISCLOSURE

The present disclosure relates to medical systems, and in particular, but not exclusively to, signal generation.

BACKGROUND

A wide range of medical procedures involve placing probes, such as catheters, within a patient's body. One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium and the heart volume, and selectively ablating cardiac tissue by application of energy. Catheters are inserted into the heart chamber and optionally around the heart chamber during such procedures. In most procedures, multiple catheters are inserted into the patient. Catheters may include mapping, ablation, temperature sensing and image sensing catheters. Some catheters are dedicated for placement in specific parts of the anatomy, e.g., coronary sinus, esophagus, atrium, ventricle. The catheters have multiple electrical channels, some more than others depending on the number of sensors and electrodes included in each catheter. The number and type of catheters depends on the procedure and on the physician preferred workflow.

BRIEF DESCRIPTION OF THE DRAWINGS

The present disclosure will be understood from the following detailed description, taken in conjunction with the drawings in which:

FIG. 3 is a flowchart including steps in a method of operation of the system of FIG. 1; and FIG. 4 is an example signal pulse for use in the system of FIG. 1.

DESCRIPTION OF EXAMPLES

Overview

Figure 1:
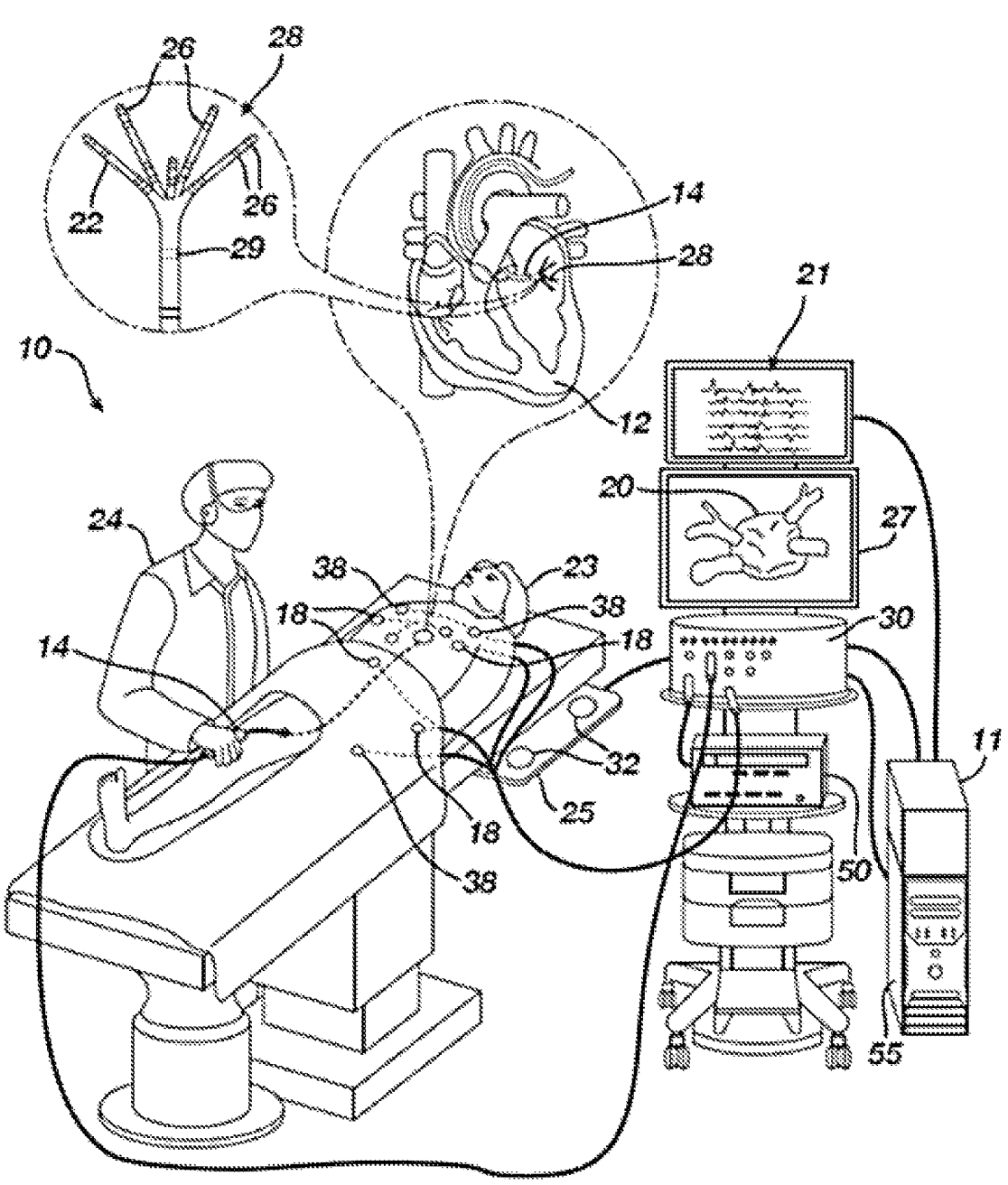
FIG. 1 is a pictorial view of a catheter-based electrophysiology mapping and ablation system constructed and operative in accordance with an exemplary mode of the present disclosure.

One method to track the position of a catheter is based on catheter electrodes transmitting position signals at different unique frequencies. The signals may be detected by body surface patches and processed by a processor, for example, based on a distribution of currents or impedances over the body surface patches, to compute the position of the catheter and/or the electrodes.

In today's generation of catheters, the number of electrodes has sharply increased. This increase would lead to an increase in the number of different unique frequency position signals, an increase in the frequency band to accommodate all the unique frequencies, and an increase in the number of frequency generators to generate these signals. To solve this problem, signals may be transmitted using time division multiplexing (TDM) so that the same signal frequency may be used for a number of electrodes while directing the signal to different ones of the electrodes during different time periods, e.g., transmit from electrode 1 during time period A, and from electrode 2 during time period B, and so on. In this manner, electrodes may be divided into groups that transmit at the same group-frequency and one electrode per group transmits at any one time. In this manner, the number of different frequencies and frequency generators is reduced. Each TDM signal per time period is typically a signal pulse with a rectangular envelope.

The same electrodes which transmit position signals also detect intracardiac electrogram (IEGMs). The transmitted TDM signal pulses, due to the non-linear surface impedance between the metal electrode and the blood pool, induce artifacts (e.g., signal spikes) in the detected IEGMs corresponding to the start and end points of the TDM bursts. A direct current (DC) signal component is also imposed on the IEGM signals throughout the TDM signal pulses.

Therefore, in accordance with an exemplary mode of the present disclosure, the TDM signal pulses are generated with non-rectangular signal envelopes thereby reducing or eliminating signal spikes in the detected IEGMs. The signal pulses are time multiplexed among electrode lines to different catheter electrodes.

The non-rectangular signal envelope may be generated with a gradual increase in a peak-to-peak amplitude of the envelope over time to a maximum peak-to-peak amplitude and then after a given time period a gradual reduction in the envelope over time to a zero (or other minimum) peak-to-peak amplitude. The gradual increase in the peak-to-peak amplitude of the envelope may be based on an error function (ERF) or other suitable function. The gradual reduction in the peak-to-peak amplitude of the envelope may be based on a complimentary error function (ERFC) or other suitable function.

In some exemplary modes, a digital signal pulse representation is retrieved from memory by a processor such as a field-programmable gate array (FPGA), which provides the retrieved digital signal pulse representation to a digital-to-analog converter (DAC), which converts the digital signal pulse representation into an analog signal including a signal pulse with the non-rectangular envelope.

The direct current (DC) signal component imposed on the IEGM signals may be reduced or eliminated by generating the signal pulses so that a maximum current density on the catheter electrodes is less than a threshold current density. The threshold current density may be determined by adjusting the amplitude of the signal pulses and examining the IEGM signals until the DC signal component is eliminated or sufficiently reduced. For iridium-platinum electrodes it is estimated that the threshold current density is about 0.44 $mA/mm^2$.

System Description

Reference is made to FIG. 1, which is a pictorial view of a catheter-based electrophysiology mapping and ablation system 10 constructed and operative in accordance with an exemplary mode of the present disclosure. System 10 includes multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, one or more catheters may be inserted into the delivery sheath catheter so as to arrive at the desired location in heart 12. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Physician 24 may place a distal tip 28 of catheter 14 in contact with the heart wall for sensing a target site in heart 12. For ablation, physician 24 may similarly place a distal end of an ablation catheter in contact with a target site for ablating tissue.

Catheter 14 is an exemplary catheter that includes one and preferably multiple electrodes 26 optionally distributed over a plurality of splines 22 at distal tip 28 and configured to sense the IEGM signals. Catheter 14 may additionally include a position sensor 29 embedded in or near distal tip 28 for tracking position and orientation of distal tip 28. Position sensor 29 may be a magnetic based position sensor including three magnetic coils for sensing three-dimensional (3D) position and orientation (including roll).

Magnetic based position sensor 29 may be operated together with a location pad 25 including a plurality of magnetic coils 32 configured to generate magnetic fields in a predefined working volume. Real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,5391,199; 5,443,489; 5,558,091; 6,172,499; 6,239,724; 6,332,089; 6,484,118; 6,618,612; 6,690,963; 6,788,967; 6,892,091.

System 10 includes one or more electrode (body surface) patches 38 positioned for skin contact on patient 23 to establish location reference for location pad 25 as well as impedance-based tracking of electrodes 26. For impedance-based tracking, electrical current is directed to electrodes 26 and sensed at electrode body surface patches 38 so that the location of each electrode can be triangulated (or otherwise computed) via the electrode patches 38. Details of the impedance-based location tracking technology are described in U.S. Pat. Nos. 7,536,218; 7,756,576; 7,848,787; 7,869,865; and 8,456,182.

A recorder 11 records and displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, other electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software stored therein, and user interface capability. Workstation 55 may provide multiple functions, optionally including (1) modeling the endocardial anatomy in three-dimensions (3D) and rendering a model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied. One commercial product embodying elements of the system 10 is available as the CARTO™3 System, available from Biosense Webster, Inc., 31A Technology Drive, Irvine, CA 92618.

Figure 2:
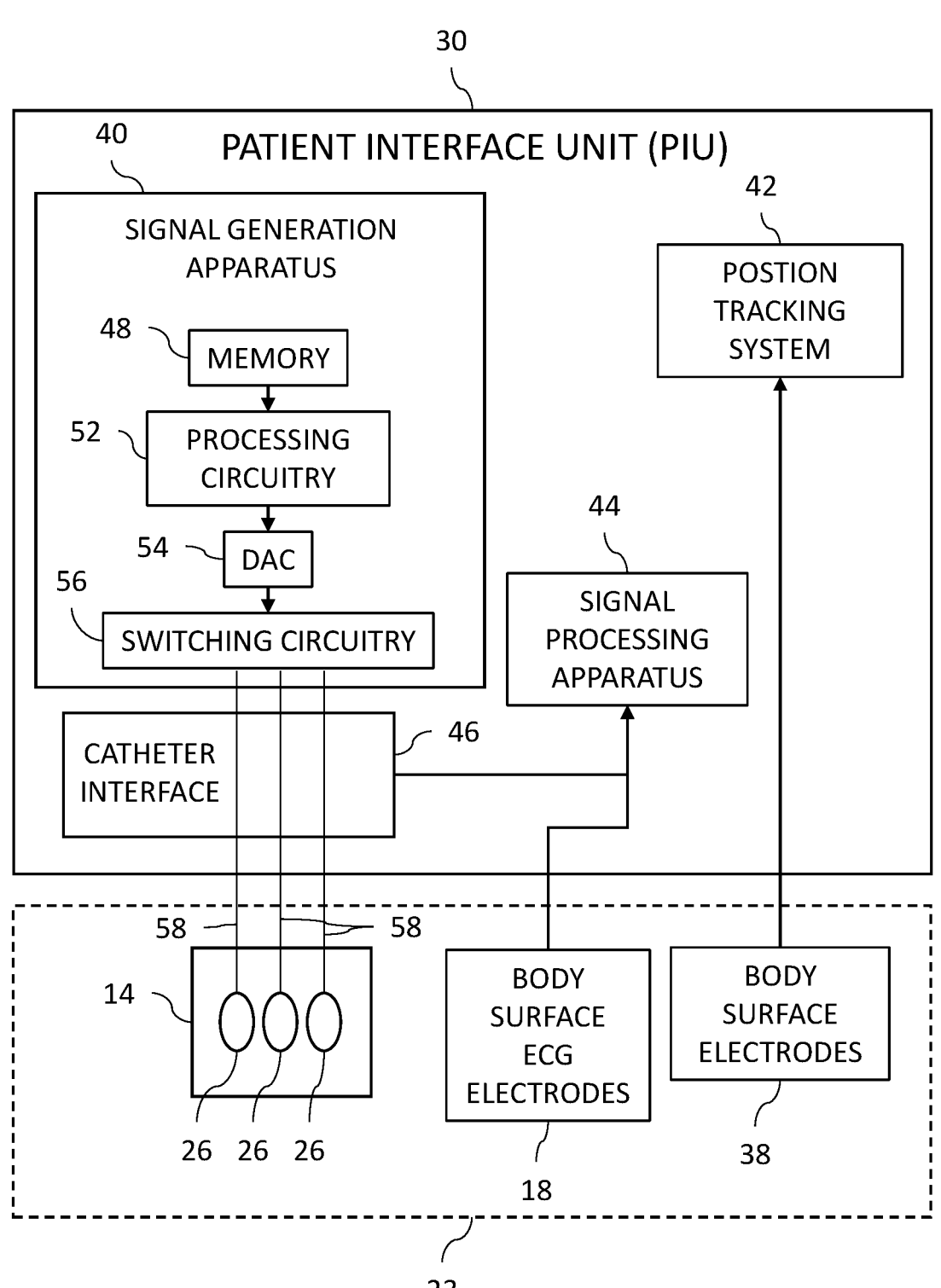
FIG. 2 is a block diagram view of a patient interface unit in the system of FIG. 1.

Reference is now made to FIG. 2, which is a block diagram view of the patient interface unit 30 in the system 10 of FIG. 1. The PIU 30 includes a signal generation apparatus 40, a position tracking system 42, a signal processing apparatus 44, and a catheter interface 46. The catheter interface 46 includes electrode lines 58 configured to be electrically connected to respective electrodes 26 of the catheter 14 via a suitable connector or connectors.

The signal generation apparatus 40 includes a memory 48, processing circuitry 52 (such as an FPGA or a suitable application-specific integrated circuit (ASIC) or a microprocessor programmed with suitable software), a digital-to-analog converter 54, and switching circuitry 56. The signal generation apparatus 40 is configured to generate signal pulses which are time multiplexed to the electrodes 26 of the catheter 14 via the electrode lines 58 of the catheter interface 46 as described in more detail with reference to FIG. 3 below.

FIG. 2 shows the catheter 14, which is configured to be inserted into a body part (e.g., the heart 12) of a living subject (e.g., the patient 23, depicted as a block in FIG. 2 for the sake of simplicity). The electrodes 26 of the catheter 14 are configured to emit position signals responsively to the time multiplexed signal pulses generated by the signal generation apparatus 40.

As described with reference to FIG. 1, electrode patches 38 (or body surface electrodes) are configured to be applied to a body surface (e.g., chest and/or back) of the living subject (e.g., the patient 23) and detect the position signals emitted by the electrodes 26 of the catheter 14. The position tracking system 42 is configured to compute a position of the catheter 14 (and/or the electrodes 26 of the catheter 14) responsively to the detected position signals, for example, responsively to a distribution of currents and/or impedances over the electrode patches 38. The position tracking system 42 identifies the electrode 26 transmitting one of the position signals based on the frequency of transmission of the detected position signal and a time period in which the position signal is detected according to a time schedule of the TDM used in system 10.

The signal processing apparatus 44 is configured to: receive electro-anatomical signals from the electrodes 26 via the electrode lines 58 and from the body surface ECG electrodes 18 and process the received electro-anatomical signals (e.g., by filtering the signals and/or computing annotation times).

Reference is now made to FIG. 3, which is a flowchart 60 including steps in a method of operation of the system 10 of FIG. 1. The signal generation apparatus 40 is configured to generate signal pulses (block 62). Each of the signal pulses includes a carrier frequency and has a non-rectangular signal envelope, described in more detail with reference to FIG. 4. The carrier frequency may have any suitable value, for example, in the range of 50-250 kHz or in the range of 100-110 kHz. The signal generation apparatus 40 is configured to time multiplex the signal pulses among the electrode lines 58 (block 64) for example using the switching circuitry 56 which switches the output of the digital-to-analog converter 54 to the different electrode lines 58 according to a time division multiplexing schedule. For example, in time period A, the output of the digital-to-analog converter 54 is connected to electrode line X, and in time period B, the output of the digital-to-analog converter 54 is connected to electrode line Y, and in each time period a whole signal pulse is generated by the digital-to-analog converter 54.

Reference is now made to FIG. 4, which is an example signal pulse 80 for use in the system 10 of FIG. 1. The signal pulse 80 includes a non-rectangular signal envelope 82, and a carrier frequency 84.

The signal generation apparatus 40 is configured to generate the non-rectangular signal envelope 82 with a gradual increase 86 in a peak-to-peak amplitude of the envelope 82 over time (t) to a maximum peak-to-peak amplitude (P) and then after a given time period a gradual reduction 88 in the envelope 82 over time (t) to a zero peak-to-peak amplitude (or a given peak-to-peak amplitude). The terms "gradual increase" and "gradual reduction" as used in the specification and claims, are defined as an increase, or decrease in the non-rectangular signal envelope 82 which occurs over time. In other words, the non-rectangular signal envelope 82 increases from a zero peak-to-peak value over time to a maximum peak-to-peak value P as the non-rectangular signal envelope 82 reaches a plateau and then decreases over time to a zero peak-to-peak value. The non-rectangular signal envelope 82 may have any suitable width $W_f$. For example, the non-rectangular signal envelope 82 may have a width in the range of 10-100 milliseconds, or in the range of 40-50 milliseconds. The width $W_i$ of the gradual increase 86 and the width $W_r$ of the gradual reduction 88 may have any suitable width. For example, $W_i$ and/or $W_r$ may have a width in the range of 50-500 microseconds, or in the range of 150-250 microseconds.

The gradual increase 86 in the peak-to-peak amplitude of the envelope 82 may be based on an error function (ERF) or any suitable function or shape. The gradual reduction 88 in the envelope 82 may be based on a complementary error function (ERFC) or any suitable function or shape.

The ERF function is defined as:

$$\text{erf}(x) = \frac{2}{\sqrt{\pi}} \int_0^x e^{-t^2} dt$$

and $$\text{ERFC} = 1 - \text{ERF}.$$

erf(x) may be computed using any suitable values of x. For example, x may be a vector of numbers between 0 to 3.5 with an increment of 0.01 (i.e., x=[0, 0.01, 0.02, 0.03, . . . 3.5]).

Reference is again made to FIG. 3. The memory 48 is configured to store a digital signal pulse representation, for example, a point-by-point representation of the signal pulse 80 of FIG. 4. The 52 is configured to retrieve the digital signal pulse representation from the memory 48 (block 66) and provide the digital signal pulse representation to the digital-to-analog converter 54 (block 68), which is configured to convert the digital signal pulse representation into an analog signal including one of the signal pulses 80 (block 70). The steps of blocks 68 and 70 are repeated to generate a series of signal pulses 80 for output to the catheter 14. The output of the digital-to-analog converter 54 is connected to the switching circuitry 56 which is controlled to connect the output of the digital-to-analog converter 54 to a selected one of the electrode lines 58 in any TDM time period according to the TDM schedule described above. The switching circuitry 56 may be controlled by the processing circuitry 52 or any suitable processor. The processing circuitry 52 also times the generation of the signal pulses 80 according to the TDM schedule so that whole signal pulses 80 are transmitted by respective electrodes 26 in each of the TDM time periods.

In some exemplary modes, the signal generation apparatus 40 is configured to generate the signal pulses 80 with a maximum peak-to-peak amplitude P so that a maximum current density on the electrodes 26 due to the signal pulses 80 is less than a given current density. By way of example, the current density may be set to be less than 0.44 mA/mm² for iridium-platinum electrodes.

In practice, some or all of the functions of the processing circuitry 52 may be combined in a single physical component or, alternatively, implemented using multiple physical components. These physical components may comprise hard-wired or programmable devices, or a combination of the two. In some examples, at least some of the functions of the processing circuitry 52 may be carried out by a programmable processor under the control of suitable software. This software may be downloaded to a device in electronic form, over a network, for example. Alternatively, or additionally, the software may be stored in tangible, non-transitory computer-readable storage media, such as optical, magnetic, or electronic memory.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 72% to 108%.

EXAMPLES

Example 1: A medical system, comprising: a catheter interface comprising electrode lines configured to be electrically connected to respective electrodes of a catheter; and a signal generation apparatus configured to generate signal pulses, each of the signal pulses comprising a carrier frequency and having a non-rectangular signal envelope, the signal generation apparatus being configured to time multiplex the signal pulses among the electrode lines.

Example 2: The system according to example 1, further comprising: the catheter, which is configured to be inserted into a body part of a living subject, the electrodes being configured to emit position signals responsively to the time multiplexed signal pulses; body surface electrodes configured to be applied to a body surface of the living subject and detect the position signals; and a position tracking system configured to compute a position of the catheter responsively to the detected position signals.

Example 3: The system according to example 1, further comprising signal processing apparatus configured to:

receive electro-anatomical signals from the electrodes via the electrode lines; and process the received electro-anatomical signals.

Example 4: The system according to example 1, wherein the signal generation apparatus is configured to generate the non-rectangular signal envelope with a gradual increase in a peak-to-peak amplitude of the envelope over time to a maximum peak-to-peak amplitude.

Example 5: The system according to example 1, wherein the signal generation apparatus is configured to generate the non-rectangular signal envelope with a gradual increase in a peak-to-peak amplitude of the envelope over time to a maximum peak-to-peak amplitude and then after a given time period a gradual reduction in the envelope over time to a zero peak-to-peak amplitude.

Example 6: The system according to example 5, wherein the gradual increase in the peak-to-peak amplitude of the envelope is based on an error function (ERF).

Example 7: The system according to example 6, wherein the gradual reduction in the envelope is based on a complementary error function (ERFC).

Example 8: The system according to example 1, further comprising a memory configured to store a digital signal pulse representation, wherein the signal generation apparatus comprises processing circuitry and a digital-to-analog converter, the processing circuitry being configured to configured to retrieve the digital signal pulse representation from the memory and provide the digital signal pulse representation to the digital-to-analog converter, which is configured to convert the digital signal pulse representation into an analog signal including one of the signal pulses.

Example 9: The system according to example 1, wherein the signal generation apparatus is configured to generate the signal pulses with a maximum peak-to-peak amplitude so that a maximum current density on the electrodes is less than a given current density.

Example 10: A medical system, comprising: a catheter interface comprising electrode lines configured to be electrically connected to respective electrodes of a catheter; and signal generation apparatus configured to generate signal pulses and time multiplex the signal pulses among the electrode lines, wherein the signal generation apparatus is configured to generate the signal pulses with a maximum peak-to-peak amplitude so that a maximum current density on the electrodes is less than a given current density.

Example 11: A computer-implemented, comprising: generating signal pulses, each of the signal pulses comprising a carrier frequency and having a non-rectangular signal envelope; and time multiplexing the signal pulses among electrode lines configured to be electrically connected to respective electrodes of a catheter.

Example 12: The method according to example 11, further comprising: the electrodes emitting position signals responsively to the time multiplexed signal pulses; body surface electrodes applied to a body surface of a living subject detecting the position signals; and computing a position of the catheter responsively to the detected position signals.

Example 13: The method according to example 11, further comprising: receiving electro-anatomical signals from the electrodes via the electrode lines; and processing the received electro-anatomical signals.

Example 14: The method according to example 11, further comprising generating the non-rectangular signal envelope with a gradual increase in a peak-to-peak amplitude of the envelope over time to a maximum peak-to-peak amplitude.

Example 15: The method according to example \11, further comprising generating the non-rectangular signal envelope with a gradual increase in a peak-to-peak amplitude of the envelope over time to a maximum peak-to-peak amplitude and then after a given time period a gradual reduction in the envelope over time to a zero peak-to-peak amplitude.

Example 16: The method according to example 15, wherein the gradual increase in the peak-to-peak amplitude of the envelope is based on an error function (ERF).

Example 17: The method according to example 16, wherein the gradual reduction in the envelope is based on a complementary error function (ERFC).

Example 18: The method according to example 11, further comprising: storing a digital signal pulse representation; retrieving the stored digital signal pulse representation; and converting the digital signal pulse representation into an analog signal including one of the signal pulses.

Example 19: The method according to example 11, wherein the generating includes generating the signal pulses with a maximum peak-to-peak amplitude so that a maximum current density on the electrodes is less than a given current density.

Example 20: A computer-implemented, comprising: generating signal pulses; and time multiplexing the signal pulses among the electrode lines configured to be electrically connected to respective electrodes of a catheter, wherein the generating includes generating the signal pulses with a maximum peak-to-peak amplitude so that a maximum current density on the electrodes is less than a given current density.

Various features of the disclosure which are, for clarity, described in the contexts of separate examples may also be provided in combination in a single example. Conversely, various features of the disclosure which are, for brevity, described in the context of a single example may also be provided separately or in any suitable sub-combination.

The examples described above are cited by way of example, and the present disclosure is not limited by what has been particularly shown and described hereinabove. Rather the scope of the disclosure includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:
   a catheter interface comprising:
      electrode lines electrically connected to respective electrodes of a catheter and body surface electrodes, the catheter being inserted into a cardiac chamber of a patient and the electrodes emitting signal pulses dedicated for sensing positions of each of the electrodes and concurrently sensing intracardiac electrogram (IEGM) signals; and
      a signal generation apparatus generating the signal pulses, each of the signal pulses comprising a carrier frequency and having a non-rectangular signal envelope, the signal generation apparatus time multiplexing the signal pulses among the electrode lines; and a position tracking system configured to sense the signal pulses on the body surface electrodes and track positions of each of the electrodes based on the signal pulses sensed, wherein the electrodes of the catheter emit the signal pulses responsively to the time multiplexed signal pulses generated by the signal generation apparatus;

wherein the signal generation apparatus generates the non-rectangular signal envelope with a gradual increase in a peak-to-peak amplitude of the envelope over time to a maximum peak-to-peak amplitude and then after a given time period a gradual reduction in the envelope over time to a zero peak-to-peak amplitude, and wherein the gradual increase in the peak-to-peak amplitude of the envelope is based on an error function (ERF), and the gradual reduction is based on a complementary error function (ERFC) thereby reducing or eliminating signal spikes in IEGM signals sensed currently with generating the signal pulses.

2. The system according to claim 1, wherein the signal generation apparatus further comprises a memory storing a digital signal pulse representation, processing circuitry and a digital-to-analog converter, the processing circuitry configured to retrieve the digital signal pulse representation from the memory and provide the digital signal pulse representation to the digital-to-analog converter, which converts the digital signal pulse representation into an analog signal including one of the signal pulses.

3. The medical system of claim 1 further comprising an ablation energy generator, wherein the ablation energy generator is configured to conduct ablation energy to one or more of the electrodes, wherein the ablation energy generator generates one or more of radio frequency energy or pulsed field ablation energy configured for ablating tissue in the cardiac chamber.

4. The medical system of claim 1 further comprising:

body surface electrocardiogram (ECG) electrodes mounted on skin of the patient and electrically coupled to the catheter interface;

wherein the catheter interface is further configured to receive and process ECG signals from the ECG electrodes concurrently with sensing the signal pulses and the IEGM signals; and a display configured to display the ECG signals and the IEGM signals as processed.

5. A computer-implemented method comprising:

generating signal pulses by a signal generation apparatus, each of the signal pulses comprising a carrier frequency and having a non-rectangular signal envelope; and time multiplexing the signal pulses among electrode lines electrically connected to respective electrodes of a catheter, the catheter inserted into a cardiac chamber of a patient and the electrodes emitting the signal pulses responsively to the time multiplexed signal pulses generated by the signal generation apparatus, sensing the signal pulses emitted by the electrodes on body surface electrodes mounted on skin of the patient;

tracking position of each of the electrodes based on the signal pulses sensed; and sensing intracardiac electrogram (IEGM) signals on the electrodes concurrently with sensing the signal pulses among electrode lines, wherein the non-rectangular signal envelope has a gradual increase in a peak-to-peak amplitude of the envelope over time to a maximum peak-to-peak amplitude and then after a given time period a gradual reduction in the envelope over time to a zero peak-to-peak amplitude, and wherein the gradual increase in the peak-to-peak amplitude of the envelope is based on an error function (ERF), and the gradual reduction is based on a complementary error function (ERFC), thereby reducing or eliminating signal spikes in the IEGM signals.

6. The method according to claim 5, further comprising:

sensing electrocardiogram (ECG) signals from ECG electrodes mounted on the skin of the patient concurrently with sensing the IEGM signals and the signal pulses; and displaying on a display device, activation sequences compiled from IEGM signals and the ECG signals.

7. The method according to claim 5, further comprising:

receiving electro-anatomical signals from the electrodes via the electrode lines; and processing the received electro-anatomical signals.

8. The method according to claim 5, further comprising:

storing a digital signal pulse representation;

retrieving the stored digital signal pulse representation; and converting the digital signal pulse representation into an analog signal including one of the signal pulses.

* * * * *